United States Patent
Leveillard et al.

(10) Patent No.: US 10,004,780 B2
(45) Date of Patent: Jun. 26, 2018

(54) METHODS AND PHARMACEUTICAL COMPOSITIONS FOR THE TREATMENT OF AGE-RELATED MACULAR DEGENERATION (AMD)

(71) Applicants: INSERM (INSTITUT NATIONAL DE LA SANTE ET DE LA RECHERCHE MEDICALE), Paris (FR); CENTRE NATIONAL DE LA RECHERCHE SCIENTIFIQUE (CNRS), Paris (FR)

(72) Inventors: Thierry Leveillard, Paris (FR); Jose-Alain Sahel, Paris (FR); Therese Cronin, Paris (FR); Leah Byrne, Paris (FR); Ram Fridlich, Paris (FR)

(73) Assignees: INSERM (INSTITUT NATIONAL DE LA SANTÉ ET DE LA RECHERCHE MÉDICALE), Paris (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days. days.

(21) Appl. No.: 14/436,121

(22) PCT Filed: Oct. 17, 2013

(86) PCT No.: PCT/EP2013/071728
§ 371 (c)(1),
(2) Date: Apr. 16, 2015

(87) PCT Pub. No.: WO2014/060517
PCT Pub. Date: Apr. 24, 2014

(65) Prior Publication Data
US 2015/0265676 A1 Sep. 24, 2015

(30) Foreign Application Priority Data

Oct. 17, 2012 (EP) .................................. 12306278

(51) Int. Cl.
| | |
|---|---|
| *A61K 48/00* | (2006.01) |
| *C07K 14/47* | (2006.01) |
| *A61K 38/17* | (2006.01) |
| *A61K 9/00* | (2006.01) |
| *C12N 9/02* | (2006.01) |

(52) U.S. Cl.
CPC ........ *A61K 38/1709* (2013.01); *A61K 9/0048* (2013.01); *A61K 48/00* (2013.01); *C07K 14/47* (2013.01); *C12N 9/0051* (2013.01)

(58) Field of Classification Search
None
See application file for complete search history.

(56) References Cited

U.S. PATENT DOCUMENTS

| | | | | |
|---|---|---|---|---|
| 9,265,813 | B2* | 2/2016 | Luo | C12N 9/0051 |
| 2012/0156221 | A1* | 6/2012 | Perrocheau | G01N 33/5058 424/172.1 |

FOREIGN PATENT DOCUMENTS

| | | |
|---|---|---|
| EP | 2 383 286 A1 | 11/2011 |
| WO | 02/081513 A2 | 10/2002 |
| WO | 2005/113586 A2 | 12/2005 |
| WO | 2013/063383 A2 | 5/2013 |

OTHER PUBLICATIONS

Totan et al. Plasma malondialdehyde and nitric oxide levels in age related macular degeneration. 2001. British Journal of Ophthamology. vol. 85, pp. 1426-1428.*
Byrne et al., "AAV-Mediated Delivery of RdCVF and RdCVFL in a Mouse Model of Retinal Degeneration", ARVO 2012 Annual Meeting Abstracts, May 7, 2012, Web, 16 pages.
Cronin et al., "The disruption of the rod-derived cone viability gene leads to photoreceptor dysfunction and susceptibility to oxidative stress", Cell Death and Differentiation, Feb. 5, 2010, pp. 1199-1120, vol. 17, No. 7.
Leveillard et al., "Rod-Derived Cone Viability Factor for Treating Blinding Diseases: From Clinic to Redox Signaling", Science Translation Medicine, Apr. 7, 2010, pp. 1-5, vol. 2, No. 26, American Association for the Advancement of Science, US.
Byrne et al., "AAV-mediated Delivery of Rod-derived Cone Viability Factor in a Mouse Model of Retinal Degeneration", ARVO Annual Meeting Abstract Search and Program Planner, May 2011, p. 1395, vol. 2011.

* cited by examiner

*Primary Examiner* — Channing S Mahatan
(74) *Attorney, Agent, or Firm* — Whitham, Curtis & Cook

(57) ABSTRACT

The present invention relates to methods and pharmaceutical compositions for the treatment of age-related macular degeneration (AMD). In particular the present invention relates to RdCVFL polypeptide or polynucleotide for use in the treatment of AMD.

6 Claims, 1 Drawing Sheet

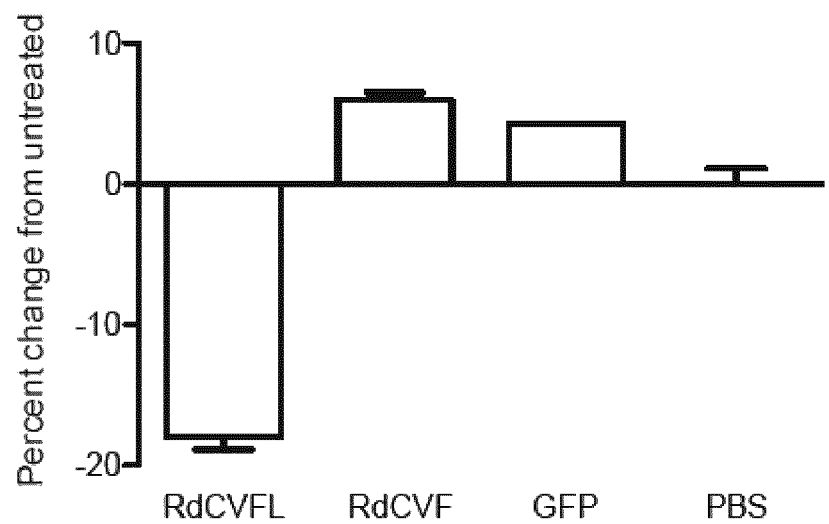

METHODS AND PHARMACEUTICAL COMPOSITIONS FOR THE TREATMENT OF AGE-RELATED MACULAR DEGENERATION (AMD)

FIELD OF THE INVENTION

The present invention relates to methods and pharmaceutical compositions for the treatment of age-related macular degeneration (AMD).

BACKGROUND OF THE INVENTION

Increased oxidative stress has been implicated in the pathogenesis of many different diseases. As a consequence of oxidative stress, proteins, lipids and DNA can be damaged, often resulting in structural changes. For example, when membrane phospholipids undergo lipid peroxidation, malondialdehyde (MDA) and other reactive decomposition products are generated. MDA and its condensation products are reliable markers for oxidative stress and have been associated with many disorders, including age-related macular degeneration (AMD), a degenerative disease affecting the retina that leads to irreversible vision loss. AMD is the principal cause of visual impairment in western countries, affecting more than 1.5 million individuals in France, eight million people in the United States. The estimated prevalence of advanced AMD is only of 0.2% at ages 55 to 64 years, but increases to 13% in those older than 85 years. A hallmark of developing AMD is the accumulation of extracellular deposits, termed drusen, which have been shown to contain MDA. Accordingly, methods that can lead to reduction of malondialdehyde (MDA) are highly desirable for the treatment of AMD.

SUMMARY OF THE INVENTION

The present invention relates to methods and pharmaceutical compositions for the treatment of age-related macular degeneration (AMD). In particular the present invention relates to RdCVFL polypeptide or polynucleotide for use in the treatment of AMD.

DETAILED DESCRIPTION OF THE INVENTION

As used herein the term "RdCVF" has its general meaning in the art and refers to rod-derived cone viability factor (Lévenlard T, Mohand-Saïd S, Lorentz O, Hicks D, Fintz A C, Clérin E et al. Identification and characterization of rod-derived cone viability factor. Nat Genet 2004; 36: 755-759.). RdCVF corresponds to a truncated thioredoxin (TRX)-like protein and is encoded by the exon 1 of the nucleoredoxin-like 1 (Nxnl1) gene. In addition to the RdCVF mRNA, the Nxnl1 gene produces a second mRNA by splicing together exons 1 and 2 to yield a longer protein isoform "RdCVFL" containing an entire TRX fold. A representative amino acid sequence of RdCVFL is accessible in GenBank under Q8VC33 accession number.

The invention relates to use, methods and pharmaceutical compositions for treating or preventing age-related macular degeneration.

In particular, gene therapy is a particularly convenient way to treat age-related macular degeneration as it enables the provision of a constant supply of a polypeptide.

Thus the invention further relates to a method for treating or preventing age-related macular degeneration which comprises the step of administering a subject in need thereof with a RdCVFL polynucleotide, i.e. a nucleic acid sequence that encodes a wild-type RdCVFL polypeptide, so that RdCVFL is expressed in vivo by the cells of the subject that have been transfected with said polynucleotide. Accordingly, said method leads to an overexpression of wild-type RdCVFL.

The invention also relates to the use of RdCVFL polynucleotide for use in the treatment of an age-related macular degeneration.

Preferably the RdCVFL polynucleotide sequence according to the invention is associated with elements that enable for regulation of its expression, such as a promoter sequence.

Such a nucleic acid may be in the form of a vector. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses (AAV)), which serve equivalent functions.

In a preferred embodiment, the expression vector is an AAV vector. Adeno-associated viral (AAV) vectors have become powerful gene delivery tools for the treatment of retinal degeneration. AAV vectors possess a number of features that render them ideally suited for retinal gene therapy, including a lack of pathogenicity, minimal immunogenicity, and the ability to transduce postmitotic cells in a stable and efficient manner. In the sheltered environment of the retina, AAV vectors are able to maintain high levels of transgene expression in the retinal pigmented epithelium (RPE), photoreceptors, or ganglion cells for long periods of time after a single treatment. Each cell type can be specifically targeted by choosing the appropriate combination of AAV serotype, promoter, and intraocular injection site.

The RdCVFL polynucleotide may be introduced into a target cell by means of any procedure known for the delivery of nucleic acids to the nucleus of cells, ex vivo, on cells in culture or removed from an animal or a subject, or in vivo.

Ex vivo introduction may be performed by any standard method well known by one skilled in the art, e.g. transfection, electroporation, iontophoresis, microinjection, transduction, cell fusion, DEAE dextran, calcium phosphate precipitation, or use of a gene gun.

The RdCVFL polynucleotide can also be introduced ex vivo or in vivo by lipofection. In certain embodiments, the use of liposomes and/or nanoparticles is contemplated for the introduction of the donor nucleic acid targeting system into host cells.

Nanocapsules can generally entrap compounds in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 Å, containing an aqueous solution in the core.

Synthetic cationic lipids designed to limit the difficulties and dangers encountered with liposome mediated transfection can be used to prepare liposomes for in vivo transfection of a gene encoding a marker. The use of cationic lipids may promote encapsulation of negatively charged nucleic acids, and also promote fusion with negatively charged cell membranes.

Alternatively, the polynucleotide of the invention may be injected directly into the vitreous, aqueous humour, ciliary body tissue(s) or cells and/or extra-ocular muscles by electroporation means Alternatively, one of the simplest and the safest way to deliver RdCVFL polynucleotide across cell membranes in vivo may involve the direct application of high concentration free or naked polynucleotides (typically mRNA or DNA). By "naked DNA (or RNA)" is meant a DNA (RNA) molecule which has not been previously complexed with other chemical moieties. Naked DNA uptake by animal cells may be increased by administering the cells simultaneously with excipients and the nucleic acid. Such excipients are reagents that enhance or increase penetration of the DNA across cellular membranes and thus delivery to the cells delivery of the therapeutic agent. Various excipients have been described in the art, such as surfactants, e.g. a surfactant selected form the group consisting of Triton X-100, sodium dodecyl sulfate, Tween 20, and Tween 80; bacterial toxins, for instance streptolysin O, cholera toxin, and recombinant modified labile toxin of $E$ $coli$; and polysaccharides, such as glucose, sucrose, fructose, or maltose, for instance, which act by disrupting the osmotic pressure in the vicinity of the cell membrane. Other methods have been described to enhance delivery of free polynucleotides, such as blocking of polynucleotide inactivation via endo- or exonucleolytic cleavage by both extra- and intracellular nucleases.

Alternatively, the invention also provides a method for treating or preventing age-related macular degeneration which comprises the step of administering a subject in need thereof with a wild-type RdCVFL polypeptide.

Knowing the amino acid sequence of the desired sequence, one skilled in the art can readily produce said polypeptides, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions.

Alternatively, the polypeptides of the invention can be synthesized by recombinant DNA techniques as is now well-known in the art. For example, these fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques.

Polypeptides of the invention can be use in an isolated (e.g., purified) form or contained in a vector, such as a membrane or lipid vesicle (e.g. a liposome).

Delivery of RdCVFL polypeptide can also be performed directly in the eye by intra vitreal injection.

Polynucleotide or polypeptide of the invention are administered to the subject in therapeutically effective amount. By a "therapeutically effective amount" of the polypeptide or polynucleotide of the invention is meant a sufficient amount of the polypeptide polynucleotide to treat AMD at a reasonable benefitrisk ratio applicable to any medical treatment. It will be understood, however, that the total daily usage of the polypeptides or polynucleotides and compositions of the present invention will be decided by the attending physician within the scope of sound medical judgment. The specific therapeutically effective dose level for any particular subject will depend upon a variety of factors including the disorder being treated and the severity of the disorder; activity of the specific polypeptide employed; the specific composition employed, the age, body weight, general health, sex and diet of the subject; the time of administration, route of administration, and rate of excretion of the specific polypeptide employed; the duration of the treatment; drugs used in combination or coincidential with the specific polypeptide employed; and like factors well known in the medical arts. For example, it is well within the skill of the art to start doses of the compound at levels lower than those required to achieve the desired therapeutic effect and to gradually increase the dosage until the desired effect is achieved.

The polypeptides or polynucleotides of the invention are typically combined with pharmaceutical acceptable carrier to form pharmaceutical composition.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

In particular, a polypeptide or polynucleotide of the invention can be delivered in a pharmaceutically acceptable ophthalmic vehicle, such that the polypeptide can penetrate the corneal and internal regions of the eye, as for example the anterior chamber, posterior chamber, vitreous body, aqueous humor, vitreous humor, cornea, irisciliary, lens, choroidretina and sclera The invention will be further illustrated by the following figures and examples. However, these examples and figures should not be interpreted in any way as limiting the scope of the present invention.

FIGURES

FIG. 1 shows the levels of the lipid peroxidation by product malondialdehyde (MDA) in rd10 retinas treated with PBS or AAV vectors comprising a polynucleotide encoding for RdCVFL, a polynucleotide encoding for RdCVF or a polynucleotide encoding for GFP.

EXAMPLE

A thiobarbituric acid reactive substances (TBARS) assay (Ohkawa, H., Ohishi, N., and Yagi, K. Assay for lipid peroxides in animal tissues by thiobarbituric acid reaction. Anal Biochem 95 351-358 (1979)). was used to determine levels of the lipid peroxidation by product malondialdehyde (MDA) in rd10 retinas treated with PBS or AAV vectors comprising a polynucleotide encoding for RdCVFL, a polynucleotide encoding for RdCVF or a polynucleotide encoding for GFP. The test was performed on three pooled retinas and was repeated three times. A representative assay is shown (FIG. 1). MDA levels were decreased by 18%±0.9% in RdCVFL-treated eyes compared to untreated eyes. Accordingly, use of RdCVFL could be suitable for the treatment of AMD wherein accumulation of MDA represents a cause of the disease.

REFERENCES

Throughout this application, various references describe the state of the art to which this invention pertains. The disclosures of these references are hereby incorporated by reference into the present disclosure.

The invention claimed is:

1. A method for reducing the accumulation of malondialdehyde (MDA) in the retina of a subject in need thereof, comprising administering to the subject a full-length rod-derived cone viability factor (RdCVFL) polynucleotide in an amount sufficient to reduce the accumulation of MDA, wherein said polynucleotide encodes a long isoform RdCVFL and does not encode a short isoform RdCVF, wherein said accumulation of MDA is reduced by at least 17 to 20%.

2. The method of claim 1 wherein the RdCVFL polynucleotide sequence is associated with at least one element that enables regulation of its expression.

3. The method of claim 2, wherein said at least one element is a promoter sequence.

4. The method of claim 1 wherein the RdCVFL polynucleotide sequence is in the form of a vector.

5. The method of claim 4 wherein the vector is an AAV vector.

6. The method of claim 1 wherein the RdCVFL polynucleotide is delivered in a pharmaceutically acceptable ophthalmic vehicle.

* * * * *